United States Patent
Aoki et al.

(10) Patent No.: US 7,900,464 B2
(45) Date of Patent: Mar. 8, 2011

(54) HUMIDITY DETECTING APPARATUS AND VEHICULAR AIR CONDITIONER HAVING THE SAME

(75) Inventors: Shinji Aoki, Chiryu (JP); Shinichirou Hirai, Ichinomiya (JP); Takuya Kataoka, Okazaki (JP); Yoshiaki Suzuki, Kariya (JP)

(73) Assignee: Denso Corporation, Kariya (JP)

( * ) Notice: Subject to any disclaimer, the term of this patent is extended or adjusted under 35 U.S.C. 154(b) by 750 days.

(21) Appl. No.: 11/900,453

(22) Filed: Sep. 12, 2007

(65) Prior Publication Data
US 2008/0066477 A1 Mar. 20, 2008

(30) Foreign Application Priority Data

Sep. 15, 2006 (JP) .................................. 2006-251561
May 17, 2007 (JP) .................................. 2007-132077

(51) Int. Cl.
*F25B 49/00* (2006.01)
*F25D 17/04* (2006.01)
*B60H 1/32* (2006.01)

(52) U.S. Cl. ........ 62/176.6; 62/150; 62/176.1; 62/228.1; 62/239; 62/244; 165/233; 236/44 R; 236/44 C; 374/142; 702/130

(58) Field of Classification Search .................. 165/233; 62/150, 239, 244, 228.1, 176.1, 176.6; 236/44 R, 236/44 C; 374/142, 208; 702/130, 133, 136

See application file for complete search history.

(56) References Cited

U.S. PATENT DOCUMENTS

| 4,920,755 A * | 5/1990 | Tadahiro | 62/176.6 |
| 6,422,062 B1 * | 7/2002 | King et al. | 62/150 |
| 2005/0178200 A1 * | 8/2005 | Stauss et al. | 73/335.02 |
| 2006/0207325 A1 | 9/2006 | Kataoka et al. | |
| 2006/0289458 A1 * | 12/2006 | Kim et al. | 219/497 |

FOREIGN PATENT DOCUMENTS

| JP | 07-179120 | 7/1995 |
| JP | 2004-191249 | 7/2004 |

* cited by examiner

*Primary Examiner* — Henry Yuen
*Assistant Examiner* — Daniel C Comings
(74) *Attorney, Agent, or Firm* — Harness, Dickey & Pierce, PLC

(57) ABSTRACT

A humidity detecting apparatus includes a humidity sensor for detecting a relative humidity of air on an inner side of a window glass, an air temperature sensor for detecting a temperature of the air, a glass temperature sensor for detecting a temperature of the window glass, and a glass surface relative humidity calculation unit for calculating a glass surface relative humidity based on output values of the humidity sensor, the air temperature sensor and the glass temperature sensor. A heat conductive member is disposed between the glass temperature sensor and the window glass.

17 Claims, 11 Drawing Sheets

HUMIDITY DETECTING APPARATUS AND VEHICULAR AIR CONDITIONER HAVING THE SAME

CROSS REFERENCE TO RELATED APPLICATION

This application is based on Japanese Patent Applications No. 2006-251561 filed on Sep. 15, 2006 and No. 2007-132077 filed on May 17, 2007, the disclosures of which are incorporated herein by reference.

FIELD OF THE INVENTION

The present invention relates to a humidity detecting apparatus and an air conditioner for a vehicle having the same.

BACKGROUND OF THE INVENTION

Generally, window fog detecting apparatuses for vehicles are mainly classified into a humidity detection type and an optical type. In the window fog detecting apparatus of the humidity detection type, for example, window fog is estimated by comparing a glass temperature with a dew-point temperature of ambient air thereof. The dew-point temperature is calculated based on outputs of a humidity sensor and an air temperature sensor, which are arranged in a passenger compartment of a vehicle.

The glass temperature is detected by various methods, such as a contact detection using a temperature sensor arranged on an inner surface of a glass, a non-contact detection using a infrared sensor, a detection based on a change of a resistance of a conductive thin film enclosed in a glass, and an estimation according to a calculation based on a vehicle outside temperature, a vehicle speed, a vehicle inside temperature and the like. The method of detection using the conductive thin film is described, for example, in Japanese Unexamined Patent Publication No. 2004-191249. The method of estimation according to the calculation is described, for example, in Japanese Patent No. 3309528.

Also, as another example of the window fog detecting apparatus of the humidity detection type, the window fog is determined by converting a relative humidity of air inside of a passenger compartment into a relative humidity on a glass surface (hereafter, a glass surface relative humidity). The fog detections described as above are performed to provide vehicles with the following effects, for example.

First, a dehumidifying operation of a refrigerant cycle of an air conditioner, that is, an operation of a compressor is performed in such a range that fog does not occur on the window glass. Therefore, the operating ratio of the dehumidifying operation is reduced, and power for driving the compressor is saved. This results in a reduction of the fuel consumption of a vehicle engine.

Second, a fog-restricting operation of the air conditioner is improved by performing the window fog determination. That is, the window fog is effectively reduced. Further, under a low temperature in winter or the like, a ratio of inside air sucked in the air conditioner is increased in such a range without causing the window fog. Thus, the ventilation heat loss is reduced and hence a heating performance of the air conditioner improves.

However, the above discussed glass temperature detections except for the contact detection using the temperature sensor are likely to increase costs. Also, detection accuracy is likely to vary due to estimation. Even in the contact detection in which the glass temperature is directly detected, a circuit board is likely to largely receive a stress depending on the mounting structure of the temperature sensor and the circuit board. Further, detection accuracy of the glass temperature is likely to be affected by contact structure between the glass surface and the temperature sensor.

SUMMARY OF THE INVENTION

In view of the above-described maters, it is an object of the present invention to provide a humidity detecting apparatus capable of accurately detecting a glass temperature without increasing stress to an internal component such as a circuit board, and an air conditioner having the humidity detecting apparatus.

According to an aspect of the present invention, a humidity detecting apparatus includes a humidity sensor for detecting a relative humidity of air on an interior side of a window glass, an air temperature sensor for detecting a temperature of the air, a glass temperature sensor for detecting a temperature of the window glass, and a glass surface relative humidity calculating unit for calculating a relative humidity of an inner surface of the window glass based on output values of the humidity sensor, the air temperature sensor and the glass temperature sensor. The humidity detecting apparatus further includes a heat conductive member between the window glass and the glass temperature sensor.

Since the heat conductive member is disposed between the window glass and the glass temperature sensor, the heat conductive member absorbs stress that will be caused when the humidity detecting apparatus is mounted to the window glass. For example, even when the sensors are soldered to a circuit board, it is less likely that soldering portions and the circuit board will be affected by the stress. Further, in a case that the glass temperature sensor is in pressed contact with the heat conductive member, heat conduction improves at contact surfaces between the glass temperature sensor and the heat conductive member. As such, the temperature of the window glass is accurately detected.

For example, the humidity detecting apparatus is employed to an air conditioner for a vehicle. The air conditioner has an inside/outside air switching device operable to open and close an inside air suction port and an outside air suction port for switching an air suction mode, a blower for blowing air drawn through at least one of the inside air suction port and the outside air suction port, a plurality of blowing-out openings for blowing air, a temperature of which has been controlled through at least one of the cooling heat exchanger and the heating heat exchanger, a blowing-out mode door operable to open and close at least a defroster blowing-out opening of the plurality of blowing-out openings for controlling an air blowing-out mode, in order to perform an air conditioning operation of a passenger compartment of the vehicle. The humidity detecting apparatus is disposed on an inner surface of a windshield of the vehicle. At least one of the inside/outside air switching device, the blower and the air blowing-out mode door is controlled based on the relative humidity calculated by the glass surface relative humidity calculation unit. Accordingly, the air conditioning operation, in particular, an anti-fog control operation is automatically performed based on the glass surface relative humidity detected by the humidity detecting apparatus. For example, the air suction mode is controlled such that an inside air ratio increases within a range without causing fog on the windshield. Thus, ventilation heat loss reduces, and hence a heating performance improves.

BRIEF DESCRIPTION OF THE DRAWINGS

Other objects, features and advantages of the present invention will become more apparent from the following detailed description made with reference to the accompanying drawings, in which like parts are designated by like reference numbers and in which.

DETAILED DESCRIPTION OF EXEMPLARY EMBODIMENTS

First Embodiment

Figure 1:
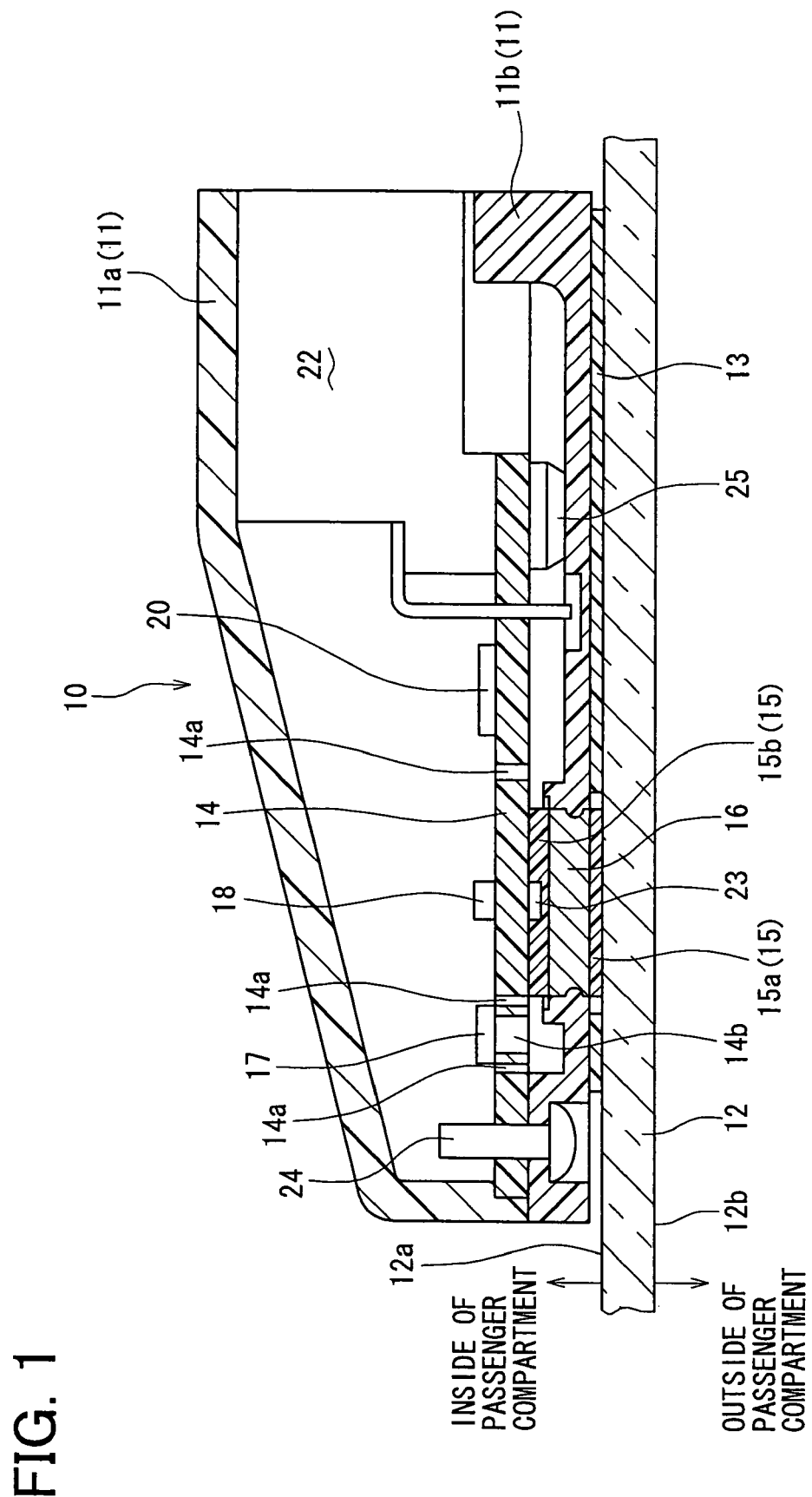
FIG. 1 is a schematic cross-sectional view of a humidity detecting apparatus according to a first embodiment of the present invention.
Figure 2:
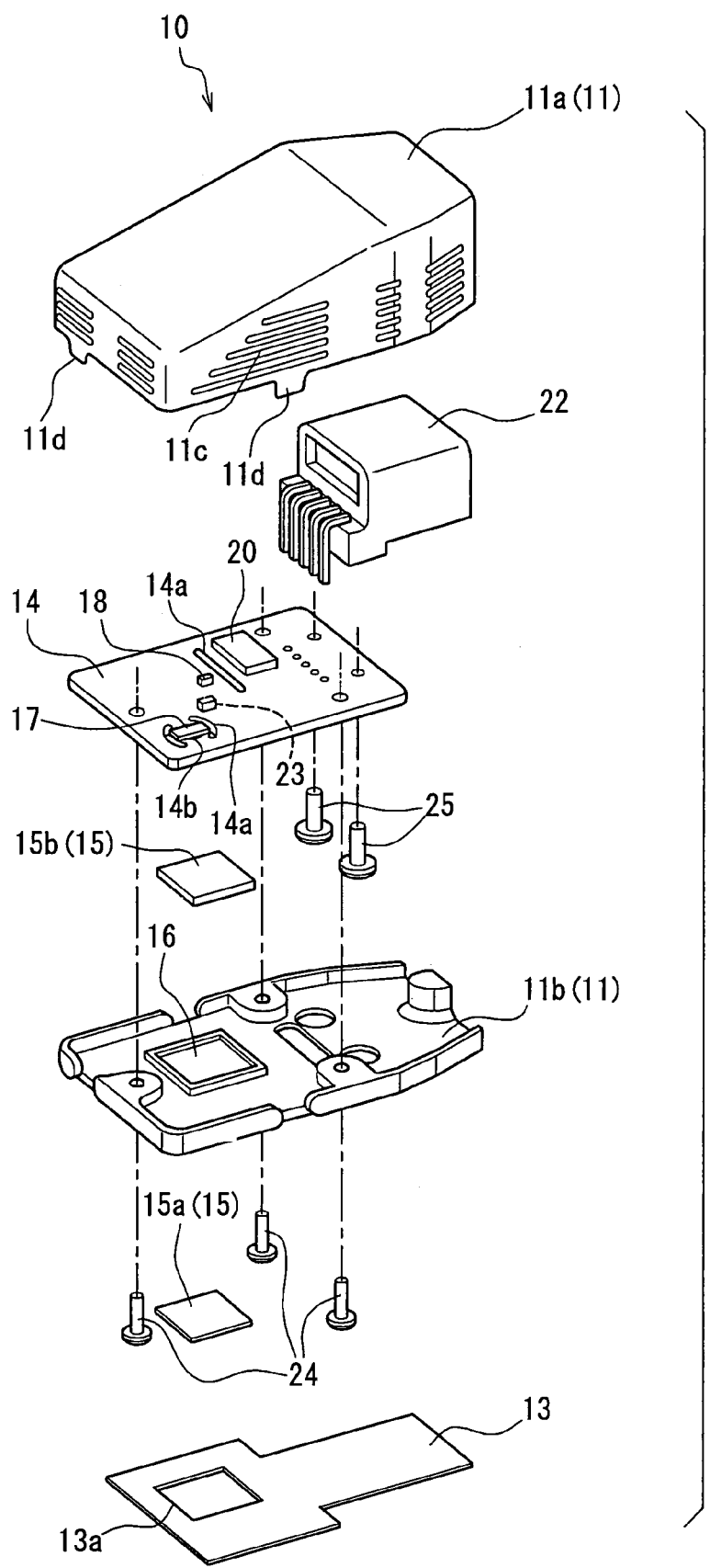
FIG. 2 is an exploded perspective view of the humidity detecting apparatus according to the first embodiment.

A first embodiment of the present invention will be described with reference to FIGS. 1 to 14. A humidity detecting apparatus 10 shown in FIGS. 1 and 2 is used, for example, for a vehicular air conditioner shown in FIG. 4.

First, a structure of the humidity detecting apparatus 10 will be described. As shown in FIGS. 1 and 2, the humidity detection apparatus 10 includes a case 11, which is, for example, made of a resin. The case 11 has a substantially flat, rectangular parallelepiped shape, and includes an upper case member 11a and a lower case member 11b. The upper case member 11a is formed with ventilation slits 11c on its side walls for allowing ambient air where the case 11 is disposed, such as air inside of a passenger compartment, to flow through the case 11.

The case 11 is fixed to an inner surface 12a of a window glass 12 of the vehicle through an adhesive sheet 13. For example, the window glass 12 is a front windshield of the vehicle, and the humidity detecting apparatus 10 is located at a position above an inside rear view mirror. In FIG. 1, numeral 12b denotes an outer surface of the window glass 12 facing outside of the vehicle.

The adhesive sheet 13 is a double-faced adhesive sheet having a thickness of approximately 0.5 mm. The adhesive sheet 13 adheres between the lower case member 11b and the inner surface 12a of the window glass 12. The adhesive sheet 13 is formed with an opening 13a on an end such that a later-described glass-side thermal conducive member 15a appears to the window glass 12.

A circuit board 14 is housed in an inner space defined between the upper case member 11a and the lower case member 11b. In the case 11, the circuit board 14 is disposed parallel to the inner surface 12a of the window glass 12.

For example, the circuit board 14 is fixed to the lower case member 11b with three screws 24. The circuit board 14 is a general printed board having conductive circuit portions on an insulated substrate. Various components, such as a glass temperature sensor 23, a humidity sensor 17, an air temperature sensor 18, an arithmetic processing unit (e.g., IC, calculation circuit unit) 20, a connector 22, amplifiers, communication circuits, and the like, are mounted on the circuit board 14.

Specifically, the humidity sensor 17, the air temperature sensor 18, the arithmetic processing unit 20 and the connector 22 are mounted to a first surface (upper surface in FIG. 1) of the circuit board 14, which faces the upper case member 11a. The glass temperature sensor 23 is mounted to a second surface (lower surface in FIG. 1) of the circuit board 14, which faces the lower case member 11b. Although not illustrated in FIGS. 1 and 2, an amplifier unit 19, a communication circuit and the like are also mounted to the first surface of the circuit board 14.

The humidity sensor 17 and the arithmetic processing unit 20 are located at positions separated from each other on the first surface of the circuit board 14, so that the humidity sensor 17 and a humidity detection environment of the humidity sensor 17 will not be affected by heat generated from the arithmetic processing unit 20. As shown in FIG. 2, for example, the humidity sensor 17 is located adjacent to a corner of the circuit board 14, and the arithmetic processing unit 20 is located at a position adjacent to a diagonally opposite corner.

The circuit board 14 is formed with a through hole 14b for improving ventilation for the humidity sensor 17. The humidity sensor 17 is arranged to extend over the through hole 14b. The circuit board 14 is also formed with slits 14a on the periphery of the humidity sensor 17 so as to restrict the heat from being transferred to the humidity sensor 17.

For example, both upper and lower sides of the humidity sensor 17 are coated with protection films, such as GORE-TEX filters. In this embodiment, the humidity sensor 17 is a capacitance variable type humidity sensor in which dielectric constant of a humidity sensitive film varies in accordance with relative humidity of air, and thus capacitance varies.

The air temperature sensor 18 and the glass temperature sensor 23 are located at a center of the circuit board 14 and close to the humidity sensor 17 as much as possible. Also, the air temperature sensor 18 and the glass temperature sensor 23 are coaxially arranged on opposite surfaces of the circuit board 14, such that a representative air temperature at a position adjacent to the inner surface 12a of the window glass 12 and a representative temperature of the inner surface 12a of the glass 12 are detected under the similar environmental condition as much as possible. For example, a thermistor, a resistance of which varies with the temperature, is used in the air temperature sensor 18 and the glass temperature sensor 23.

On the circuit board 14, another slit 14a is formed between the arithmetic processing unit 20 and the air temperature sensor 18 and glass temperature sensor 23 for restricting the heat of the arithmetic processing unit 20 from being transferred to the air temperature sensor 18 and glass temperature sensor 23 through the circuit board 14. In an example shown in FIG. 2, the slit 14a between the arithmetic processing unit 20 and the air temperature sensor 18 and glass temperature sensor 23 has a straight shape. Alternatively, the slit 14a may be formed to surround the air temperature sensor 18 and the glass temperature sensor 23.

The connector 22 is fixed to the circuit board 14 with two screws 25, for example. Further, terminals of the connector 22 are soldered with the conductive circuit portions of the circuit board 14. Thus, the connector 22 electrically connect the electric circuit portions of the circuit board 14, such as the amplifier unit 19, the calculation circuit unit 20 and the communication circuit 21, and external circuits, such as an air conditioning control unit 26 of FIG. 4 and a battery of the vehicle.

A thin metallic member 16 having high heat conductivity is integrally molded into the lower case member 11b, such as by insert-molding, at a position corresponding to the glass temperature sensor 23. For example, the metallic member 16 is a copper plate having the thickness of 2 mm. Further, heat conductive member 15 is adhered with both surfaces of the metallic plate 16. The heat conductive member 15 has high heat conductivity, and a coefficient of thermal conductivity thereof is in a range between 3 and 10 W/m·K, for example.

The heat conductive member 15 is made of a heat conductive sheet, heat conductive gel, heat conductive grease, or the like. Specifically, the heat conductive member 15 includes a glass-side heat conductive member (first heat conductive layer) 15a and a sensor-side heat conductive member (second heat conductive layer) 15b.

The glass-side heat conductive member 15a is disposed on a second side of the metallic member 16, the second side facing the inner surface 12a of the window glass 12. The glass-side heat conductive member 15a has the thickness of 0.6 mm. The sensor-side heat conductive member 15b is disposed on a first side of the metallic ember 16, the first side being opposed to the second side. The sensor-side heat conductive member 15b has the thickness of 0.8 mm.

When the circuit board 14 is fixed to the second case member 11b, the glass temperature sensor 23 is pressed into contact with the sensor-side heat conductive member 15b so that the glass temperature sensor 23 is slightly embedded in the sensor-side heat conductive member 15b. The thickness of the glass-side heat conductive member 15a is slightly larger than the thickness of the adhesive sheet 13. Therefore, a top surface of the glass-side heat conductive member 15a is slightly risen from a top surface of the adhesive sheet 13. When the humidity detecting apparatus 10 is adhered to the inner surface 12a of the window glass 12, the glass-side heat conductive member 15a is sufficiently pressed against the inner surface 12a of the window glass 12.

The temperature of the window glass 12 is transferred to the glass temperature sensor 23 through the glass-side heat conductive member 15a, the metallic member 16 and the sensor-side heat conductive member 15b. As such, the temperature of the window glass 12 is detected by the glass temperature sensor 23.

The upper case member 11a has engagement pieces 11d extending from ends of the side walls thereof to be engaged with predetermined portions of the lower case member 11b. The upper case member 11a is fixed to the lower case member 11b with the engagement of the engagement pieces 11d while pressing the circuit board 14 against the lower case member 11b.

Figure 3:
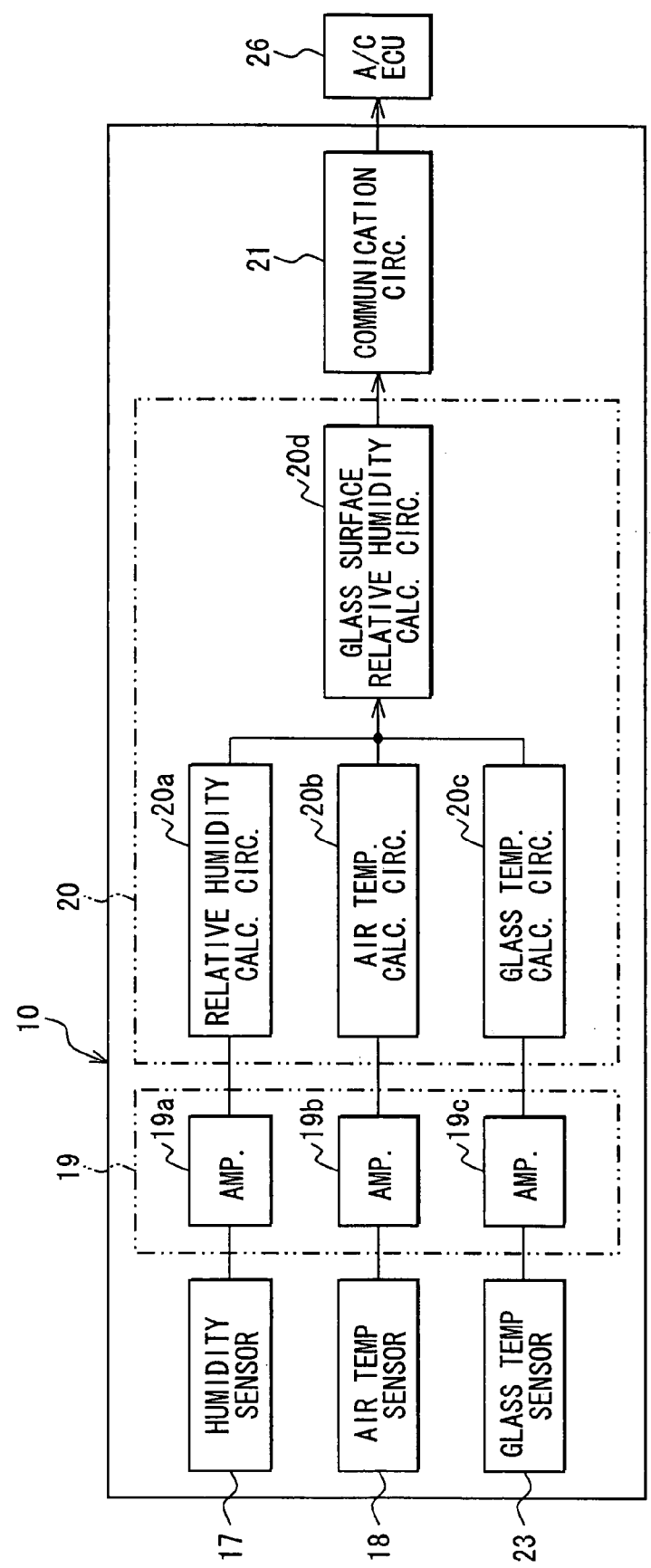
FIG. 3 is an electrical block diagram of the humidity detecting apparatus according to the first embodiment.

Next, an electrical control system of the humidity detecting apparatus 10 will be described with reference to FIG. 3. As shown in FIG. 3, the electrical control system generally includes the amplifier unit 19 and the calculation circuit unit 20. Specifically, signals outputted from the humidity sensor 17, the air temperature sensor 18 and the glass temperature sensor 23 are amplified by amplifiers 19a, 19b, 19c and then inputted to a relative humidity calculation circuit 20a, an air temperature calculation circuit 20b, and a glass temperature calculation circuit 20c, respectively.

Then, a glass surface relative humidity is calculated in a glass surface relative humidity circuit 20d based on the calculated values outputted from the calculation circuits 20a, 20b, 20c. A calculated value of the glass surface relative humidity calculation circuit 20d is outputted to the air conditioning control unit (a/c ECU) 26.

Figure 4:
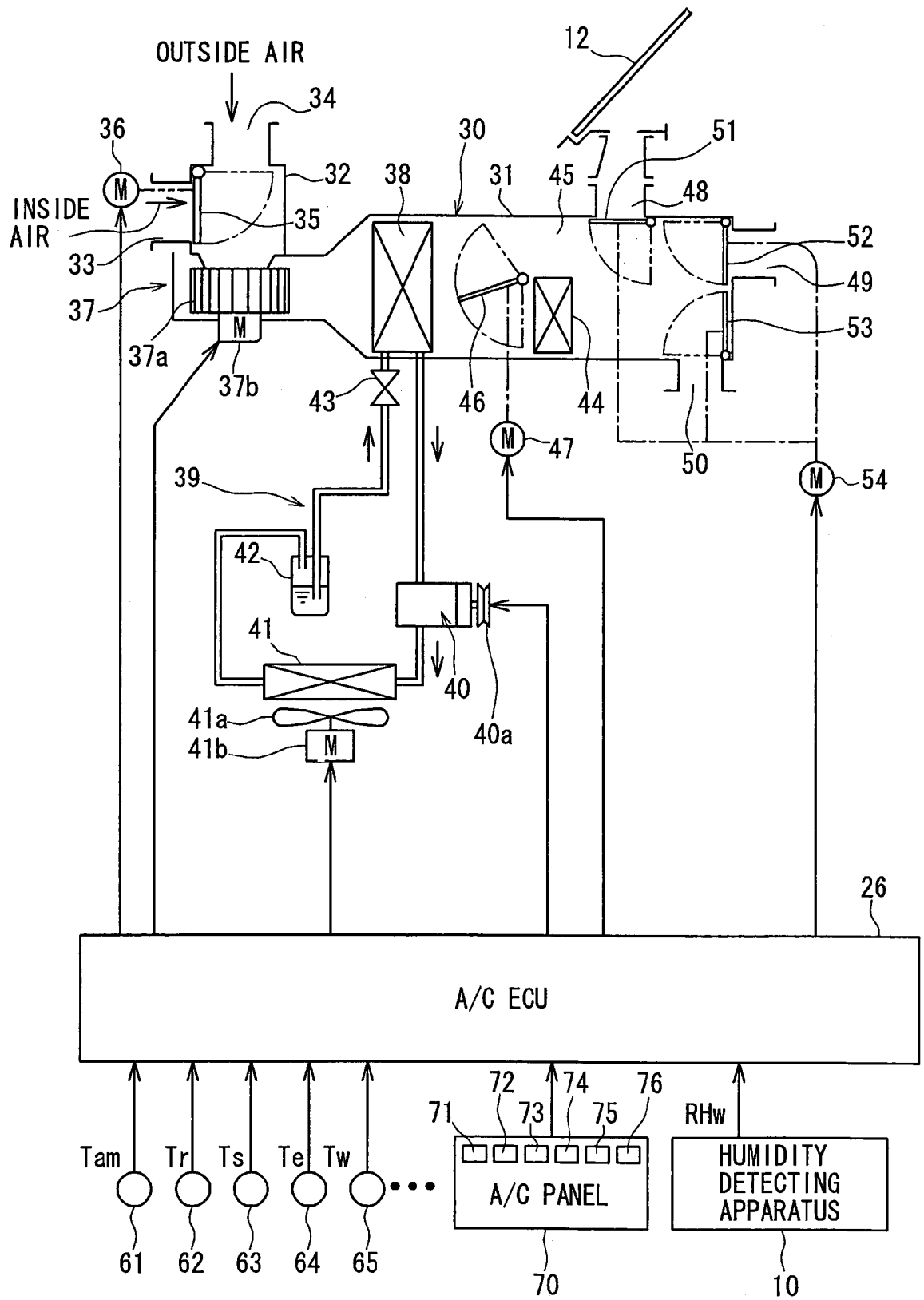
FIG. 4 is a schematic diagram showing a whole construction of a vehicular air conditioner including the humidity detecting apparatus according to the first embodiment.

Next, a whole system of the vehicular air conditioner will be described with reference to FIG. 4. An interior unit 30 of the air conditioner (hereafter, the a/c interior unit) is mounted inside of an instrument panel of the vehicle at a front part of the passenger compartment, for example. The a/c interior unit 30 has an air conditioner case 31 that defines an air passage through which air to be blown into the passenger compartment flows.

An inside/outside air switching box 32 is arranged at an upstream position of the air passage of the air conditioner case 31. The inside/outside air switching box 32 has an inside air suction port 33 for drawing the inside air and an outside air suction port for drawing air outside of the passenger compartment (outside air). The inside/outside air switching box 32 further has an inside/outside air switching door 35 as an inside/outside air switching device for selectively opening and closing the inside air suction port 33 and the outside air suction port 34. The inside/outside air switching door 35 is driven by a driving device 36, such as a servomotor.

A blower 37 of, for example, a motor-driven type, is arranged downstream of the inside/outside air switching box 32 with respect to the flow of air, to blow air drawn from the inside/outside air switching box 32 toward the passenger compartment. The blower 37 has a multi-blade centrifugal fan 37a and a motor 37b for driving the fan 37a.

An evaporator 38 as a cooling heat exchanger for cooling the air blown by the blower 37 is arranged downstream of the blower 37 in the air conditioner case 31 with respect to the flow of air. The evaporator 38 is one of devices of a refrigerating cycle system 39, and a low temperature, low pressure refrigerant flows inside of the evaporator 38. While flowing inside of the evaporator 38, the refrigerant absorbs heat from the air flowing outside of the evaporator 38 and evaporates, thereby cooling the air.

For example, the refrigerating cycle system 39 further has a compressor 40, a condenser 41, a fluid receiver 42, an expansion valve 43 as a decompressing device and the like. In the refrigerating cycle system, the refrigerant flows from a discharge side of the compressor 40 to the evaporator 38 through the condenser 41, the receiver 42 and the expansion valve 43 and returns to the compressor 40 from the evaporator 38.

The condenser 41 is disposed such that outside air as cooling air passes through the condenser 41. For example, a flow of the outside air is created by a cooling fan 41a, which is driven by a motor 41b. The compressor 40 is driven by a vehicle engine (not shown) through an electromagnetic clutch 40a. Thus, the operation of the compressor 40 can be intermittently controlled by intermittently supplying power to the electromagnetic clutch 40a.

In the a/c interior unit 30, a heater core 44 is disposed downstream of the evaporator 38 with respect to the flow of air in the air conditioner case 31. The heater core 30 is a heating heat exchanger for heating the air that has passed through the evaporator 38 using heat of an engine coolant, which flows inside of the heater core 30. A bypass passage 45 is formed in the air conditioner case 31 beside the heater core 44 to allow the air that has passed through the evaporator 38 to bypass the heater core 44.

An air mixing door 46 as a temperature controlling member is rotatably arranged between the evaporator 38 and the heater core 44. The air mixing door 46 is driven by a driving device 47, such as a servomotor. A position or an open degree of the air mixing door 46 is adjusted by the driving device 47.

A ratio of the volume of air flowing toward the heater core 44 to be heated to the volume of air flowing into the bypass passage 45 is adjusted according to the position of the air mixing door 46. Thus, a temperature of air blown into the passenger compartment is adjusted by the air mixing door 46.

The air conditioner case 31 has a defroster air-blowing opening 48, a face air-blowing opening 49, a foot air-blowing opening 50 at a downstream position thereof with respect to the flow of air. The air passing through the defroster air-blowing opening 48 is blown toward the windshield 12. The air passing through the face air-blowing opening 49 is blown toward an upper area of the passenger compartment, such as a face area of a passenger. The air passing through the foot air-blowing opening 50 is blown toward a lower area of the passenger compartment, such as a foot area of a passenger.

A defroster door 51, a face door 52 and a foot door 53 are rotatably supported at positions upstream of the defroster air-blowing opening 48, the face air-blowing opening 49 and the door air-blowing opening 50, respectively. The defroster door 51, the face door 52 and the foot door 53 are provided as air-blowing-out mode doors and are operated by a driving device 54 such as a servomotor through a link mechanism (not shown).

The air conditioning control unit 26 is constructed of a well-known microcomputer and peripheral circuits thereof. The microcomputer has a CPU, a ROM, a RAM and the like. A control program for an air conditioning control operation is beforehand memorized in the ROM, and the air conditioning control unit 26 executes various calculations and processing operations based on the memorized control program.

The calculation value of the humidity detecting apparatus 10 is inputted to the air conditioning control unit 26. Also, detection signals from well-known air conditioner sensors such as an outside air sensor 61, an inside air sensor 62, a solar radiation sensor 63, an evaporator temperature sensor 64, and a water temperature sensor 65 are inputted to the air conditioning control unit 26. Further, operation signals from an air conditioning operation panel 70 are inputted to the air conditioning control unit 26.

Specifically, the outside air sensor 61 detects a temperature of air outside of the passenger compartment (hereafter, the outside air temperature Tam). The inside air sensor 62 detects a temperature of air inside of the passenger compartment (hereafter, the inside air temperature Tr). The solar radiation sensor 63 detects the amount of solar radiation entering the passenger compartment (hereafter, the solar radiation amount Ts). The evaporator temperature sensor 64 is arranged at an air blowing-out portion of the evaporator 38 to detect a temperature of air flowing out from the evaporator 38 (hereafter, the evaporator blowing-out air temperature Te). The water temperature sensor 65 detects a temperature of heated fluid (hereafter, the heated fluid temperature Tw), such as an engine coolant, which flows through the heater core 44.

The air conditioning operation panel 70 is provided thereon with various air conditioner operating members, such as a temperature setting switch 71, a blowing-out mode switch 72, an inside/outside air selecting switch 73, an air conditioning switch 74, a blower actuation switch 75, and an automatic switch 76.

The temperature setting switch 71 is provided as a temperature setting member for setting the inside air temperature of the passenger compartment. The blowing-out mode switch 72 is provided to manually set blowing-out modes, which are selectively switched through the blowing-out mode doors 51 to 53. The inside/outside air selecting switch 73 is provided to manually set inside/outside air suction modes through the inside/outside air switching door 35. The air conditioning switch 74 is provided to output an actuation command signal of the compressor 40, such as ON signal of electromagnetic clutch 40a. The blower actuation switch 75 is provided to manually set the volume of air blown by the blower 37. The automatic switch 76 is provided to output a command signal of an air-conditioner automatic control state.

The electromagnetic clutch 40a of the compressor 40, the electrical driving devices 36, 47, 54, the motor 37b of the blower 37, the motor 41b of the condenser cooling fan 41a and the like are connected to the output side of the air conditioning control unit 26 to be controlled based on output signals of the air conditioning control unit 26.

Next, an operation of the air conditioner according to the first embodiment will now be described.

First, the operation of the a/c interior unit 30 is described. When the blower 37 is actuated, air is drawn in the inside/outside air switching box 32 from the inside air introduction port 33 or the outside introduction port 34 and is blown into the a/c case 31. Also, as the electromagnetic clutch 40a is energized to become a connected state, and the compressor 40 is driven through the vehicle engine, the refrigerant circulates in the refrigerant cycle system 39.

In the a/c/ interior unit 30, the air blown by the blower 37 firstly passes through the evaporator 38 to be cooled and dehumidified. Then, the cooled air is divided into an air flow that flows toward the heater core 44 the be heated and an air flow that flows into the bypass passage 45, according to the position of the air mixing door 46.

Here, a ratio of the amount of air (heated air) passing through the heater core 44 to the amount of air (cooled air) flowing through the bypass passage 45 is adjusted according to the position of the air mixing door 46. Therefore, the temperature of air to be blown into the passenger compartment is controlled.

The conditioned air, the temperature of which has been controlled, is blown into the passenger compartment through at least one of the defroster blowing-out port 48, the face blowing-out port 49 and the foot blowing-out port 50. Accordingly, the air conditioning operation of the passenger compartment and the anti-fog operation of the windshield 12 are performed.

Next, an operation of the humidity detecting apparatus 10 according to the first embodiment will be described with reference to FIG. 5.

Figure 5:
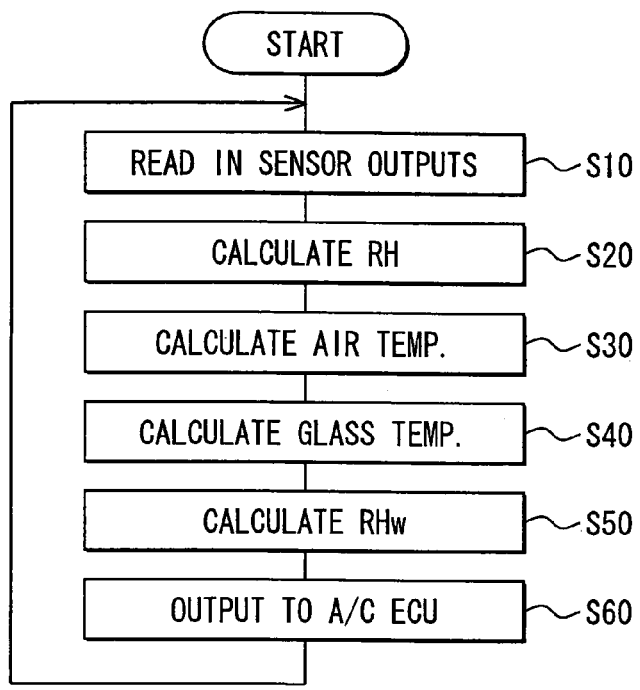
FIG. 5 is a flow chart showing a calculation processing executed by a calculation circuit in FIG. 3.

FIG. 5 shows a control routine executed by the calculation circuit 20 shown in FIG. 3. First, at step S10, output values of the sensors 17, 18, 23, which have been amplified by amplifiers 19*a* to 19*c* shown in FIG. 3, are read in. Next, at step S20, relative humidity RH of the inside air near the window glass 12 is calculated based on an output value V of the humidity sensor 17.

That is, a predetermined calculation formula (I) as shown below is predetermined for converting the output value V of the humidity sensor 17 to the relative humidity RH. The relative humidity RH is calculated by applying the output value V to the calculation formula (1).

$$RH = \alpha V + \beta \quad (1)$$

In the formula (1), $\alpha$ is a control coefficient, and $\beta$ is a constant.

Next, at step S30, the temperature of inside air near the window glass 12 is calculated by applying the output value of the air temperature sensor 18 to a predetermined calculation formula, which is set beforehand. Then, at step S40, a window glass temperature, that is, temperature of the inner surface 12*a* of the window glass 12, is calculated by applying the output value of the glass temperature sensor 23 to a predetermined calculation formula, which is set beforehand.

At step S50, a window glass surface relative humidity RHw, that is, relative humidity of the inner surface 12*a* of window glass 12, is calculated based on the relative humidity RH, the air temperature and the window glass temperature, which are calculated at steps S20-S40. Here, according to a moist air diagram, the window glass surface relative humidity RHw can be calculated based on the relative humidity RH, the air temperature, and the window glass temperature. Then, at step S60, the value of the window glass surface relative humidity RHw is outputted to the air conditioning control unit 26.

Figure 6:
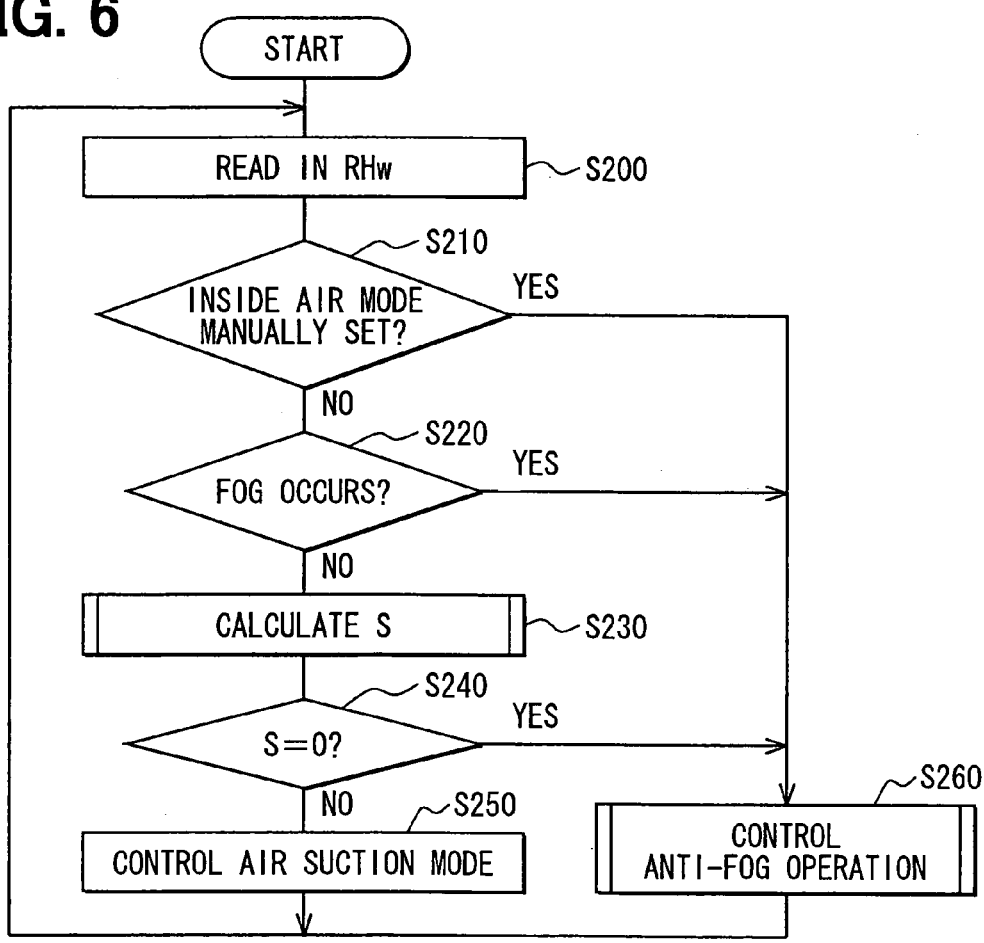
FIG. 6 is a flow chart showing exemplary basic logic of a control of the air conditioner according to the first embodiment.

Next, an air conditioning control operation based on the window glass surface relative humidity RHw will be described with reference to FIG. 6. FIG. 6 shows a control routine showing a basic logic of the control of the air conditioner.

First, at step S200, the window glass surface relative humidity RHw calculated according to the control routine of FIG. 5 is read in. Next, at step S210, it is determined whether or not the inside/outside air suction mode is manually set in the inside air mode via the inside/outside air selecting switch 73 of the air conditioning operation panel 70. When it is determined that the inside/outside air suction mode is not manually set in the inside air mode, that is, result of step S210 is "NO", it is further determined, at step S230, whether or not the window fog occurs based on the window glass surface relative humidity RHw. When the result is "NO" in step S220, an inside/outside air control instruction value S is calculated at step S230.

Figure 7:
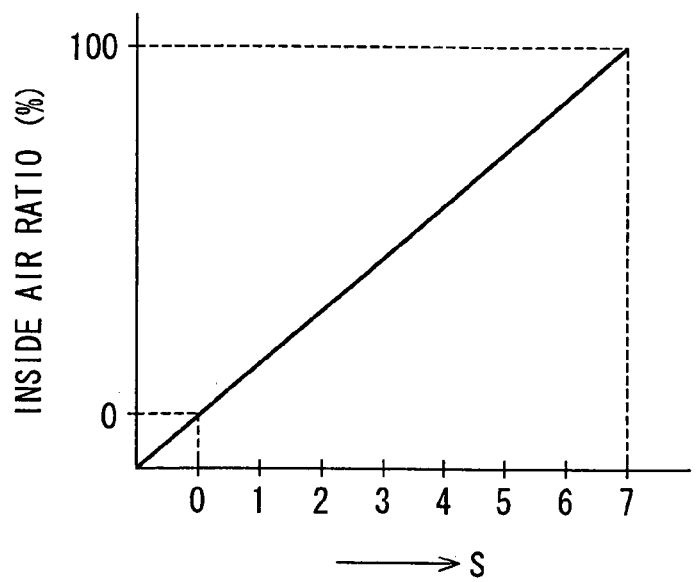
FIG. 7 is a characteristic diagram showing a relationship between an inside/outside air control instruction value and an inside air ratio according to the first embodiment.

FIG. 7 is a characteristic diagram for showing a relationship between the inside/outside air control instruction value S and an inside air ratio. The inside air ratio is a ratio of the inside air to the air drawn in the air conditioner. As shown in FIG. 7, the inside/outside air control instruction value S is a value for determining the inside air ratio.

In FIG. 7, when the inside/outside air control instruction value S is zero, the inside air ratio is set to 0%, that is, set to the outside air mode where 100% of suction air is outside air. When the inside/outside air control instruction value S is seven, the inside air ratio is set to 100%, that is, set to the inside air mode where 100% of suction air is inside air. The inside air ratio sequentially increases with an increase in the inside/outside air control instruction value S from one to seven.

Figure 8:
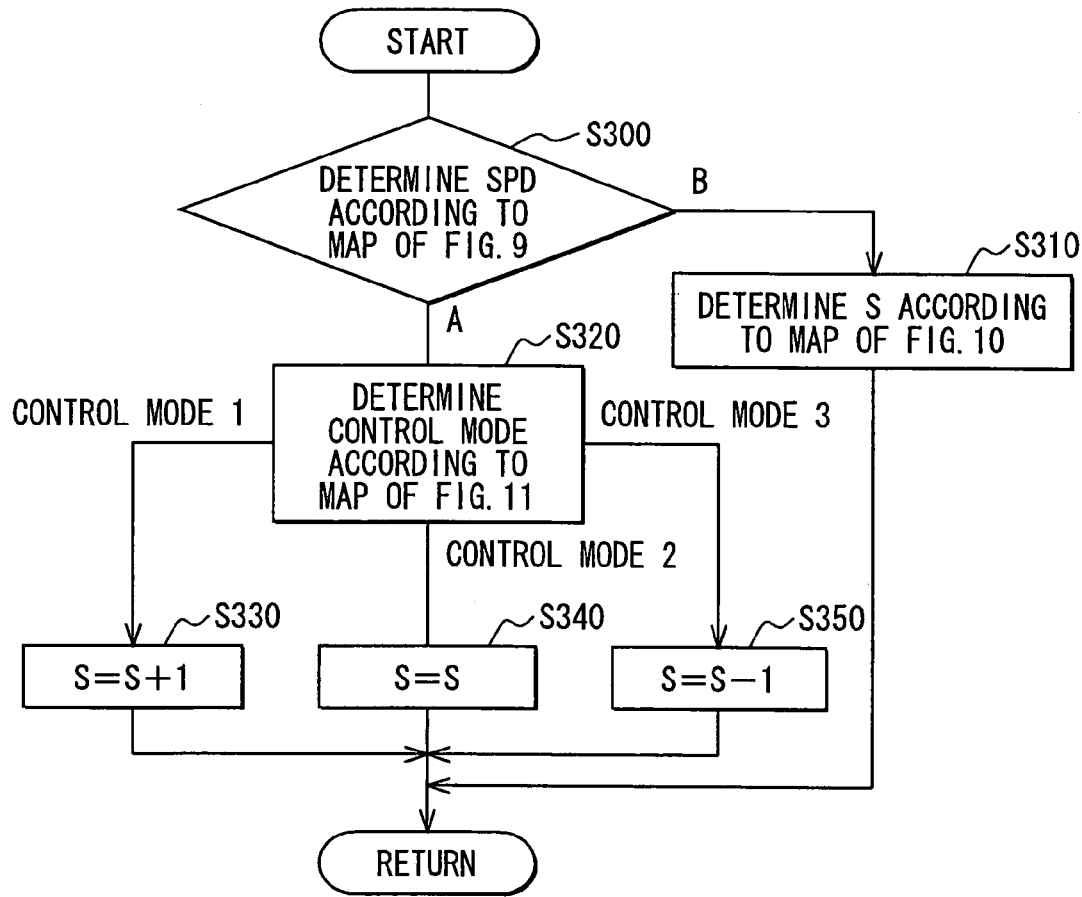
FIG. 8 is a flow chart showing exemplary logic of an inside/outside air control according to the first embodiment.
Figure 9:
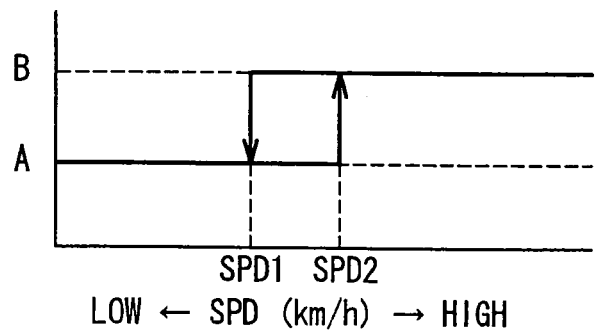
FIG. 9 is a characteristic diagram showing a vehicle speed determining operation for the inside/outside air control according to the first embodiment.

FIG. 8 shows an example of a control routine performed at step S230. First, at step S300, it is determined whether a vehicle speed SPD is in a low speed area A or in a high speed area B based on a map shown in FIG. 9. When it is determined that the vehicle speed SPD is in the high speed area B, the inside/outside air control instruction value S is determined, at step S310, based on the window glass surface relative humidity RHw as indicated in a map of FIG. 10.

Figure 10:
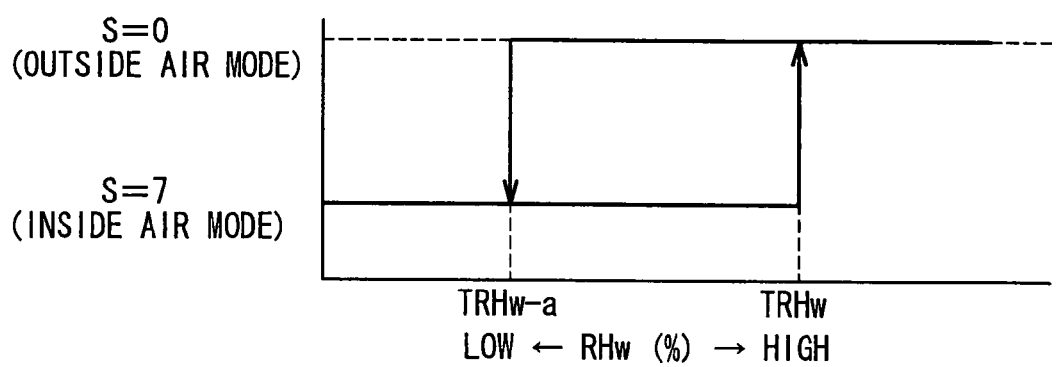
FIG. 10 is a characteristic diagram showing a relationship between a window glass surface relative humidity and the inside/outside air control instruction value (inside/outside air suction mode) according to the first embodiment.

As shown in FIG. 10, in a case where the window glass surface relative humidity RHw is higher than a predetermined target window glass surface relative humidity TRHw, the inside/outside air control instruction value S is set to zero, that is, the outside air mode is set. In a case where the window glass surface relative humidity RHw is lower than humidity TRHw-a, the inside/outside air control instruction value S is se to seven, that is, the inside air mode is set. Here, the target window glass surface relative humidity TRHw is a relative humidity in which fog of the window glass 12 is sufficiently restricted. The target window glass surface relative humidity TRHw is, for example, about 85%.

Figure 11:
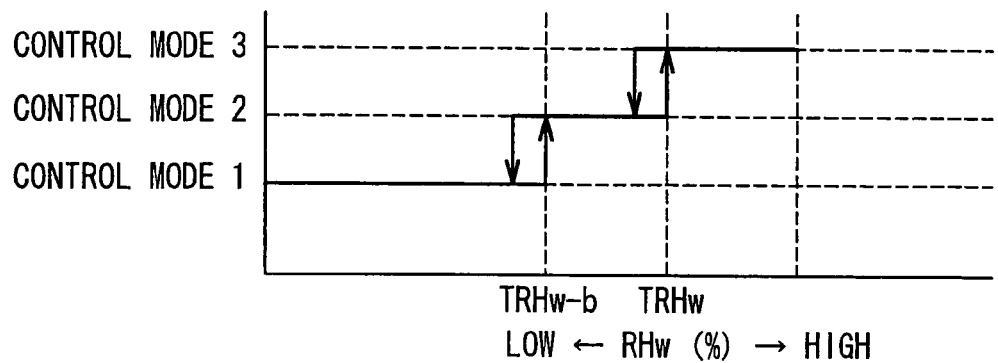
FIG. 11 is a characteristic diagram showing a relationship between the window glass surface relative humidity and inside/outside air control modes according to the first embodiment.

On the other hand, when it is determined that the vehicle speed SPD is in the low speed area A at step S300, a control mode is determined to one of control modes 1, 2 and 3 shown in the map of FIG. 11 based on the window glass surface relative humidity RHw at step S320.

As shown in FIG. 11, when the window glass surface relative humidity RHw is higher than the predetermined target window glass surface relative humidity TRHw (for example, 85%), the control mode 3 is determined. When the window glass surface relative humidity RHw is between the target window glass surface relative humidity TRHw and humidity TRHw-b, the control mode 2 is determined. When the window glass surface relative humidity RHw is lower than the humidity TRHw-b, the control mode 1 is determined.

In the case where the control mode 1 is determined at step S320, a control processing of S=S+1 is performed at predetermined time intervals at step S330. That is, the control processing is performed so that the value of the inside/outside air control instruction value S is successively increased by adding one as every predetermined time period elapses. Thus, the inside air ratio is provided with a sequential increase with a predetermined rate.

In the case where the control mode 2 is determined at step S320, because the window glass surface relative humidity RHw is approximate to the target window glass surface relative humidity TRHw, a control process of S=S is performed at step S340. That is, the previously calculated value of S is maintained as the value of the inside/outside air control instruction value S.

In the case where the control mode 3 is determined at step S320, a control process of S=S−1 is performed at predetermined time intervals at step S350. That is, the value of the inside/outside air control instruction value S is successively decreased by subtracting one therefrom as every predetermined time period elapses. Thus, the inside air ratio is provided with a sequential decrease with a predetermined rate.

The values "a" and "b" of the humidity TRHw-a and the humidity TRHw-b shown in FIG. 10 and FIG. 11 are predetermined values provided to set a hysteresis width to avoid a hunting of the inside/outside air control operation.

Then, the processing proceeds to step S240 of FIG. 6, and it is determined whether or not the above-described inside/outside air control instruction value S is equal to the value indicative of the outside air mode (i.e., S=0). When it is determined that the inside/outside air control instruction value S is not zero at step S240, the position of the inside/outside air switching door 35, that is, the inside/outside air suction mode is controlled so that the inside air ratio becomes a ratio based on the value of the inside/outside air control instruction value S.

In the inside/outside air suction mode control, since the target window glass surface relative humidity TRHw is set substantially equal to an upper limit humidity at which fog does not occur at the window glass 12, the inside/outside air suction mode can be controlled in such a manner that the inside air ratio currently becomes high, that is, within a range where fog does not occur at the window glass 12. Therefore, in a cold climate, such as in winter, when the heating operation is started, the inside air ratio is increased. As a result, ventilation thermal loss reduces, and thus a warming-up effect of the heating of the passenger compartment improves.

On the other hand, in the cases where the determination results of steps S210, S220, S240 of FIG. 6 are "YES", a fog-preventing control operation of the window glass 12 is highly required. In these cases, therefore, the anti-fog control of the window glass 12 is performed at step S260.

Figure 12:
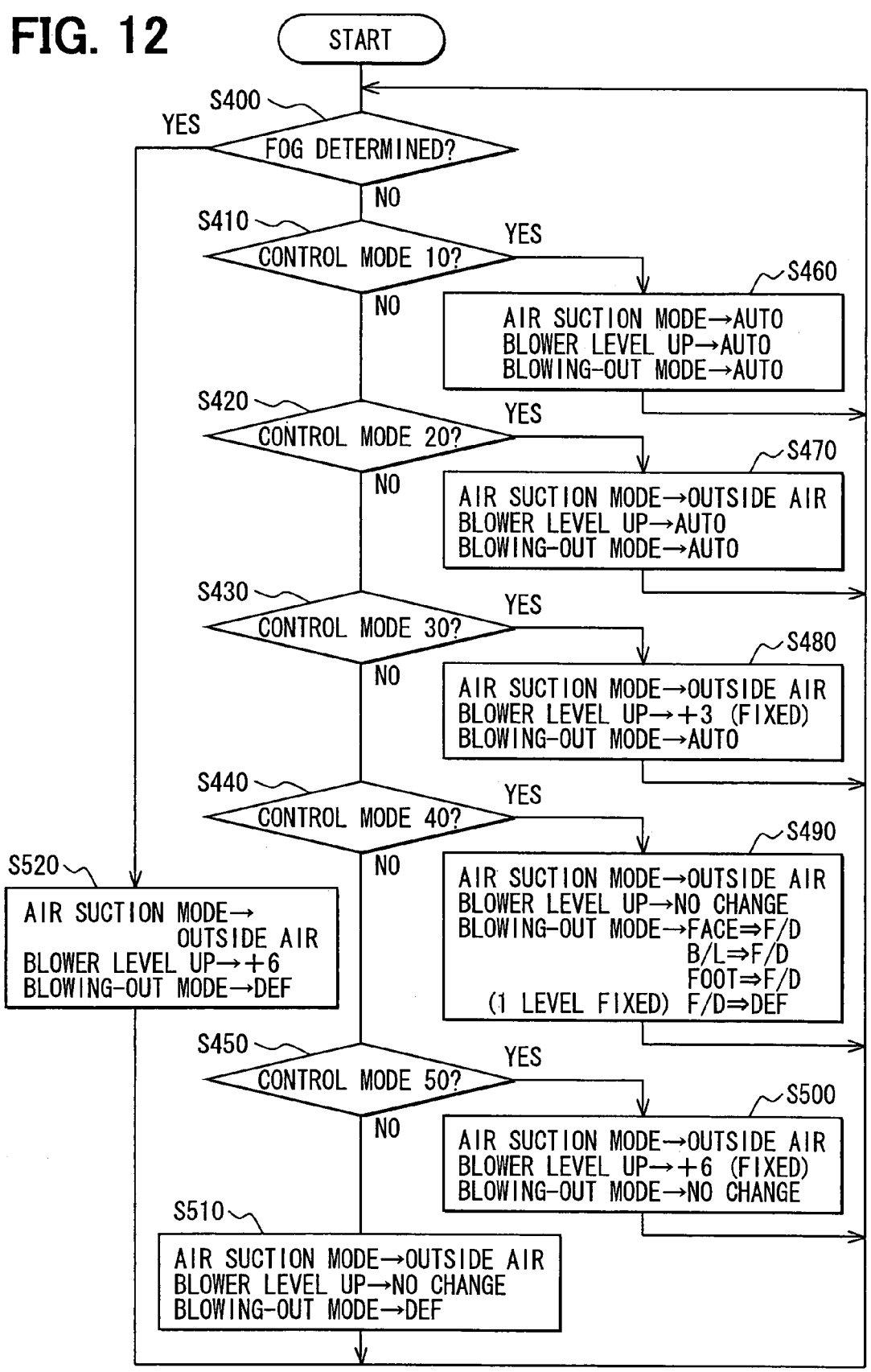
FIG. 12 is a flow chart showing exemplary logic of an anti-fog control according to the first embodiment.

FIG. 12 shows an example of a control routine of the anti-fog control operation. First, at step S400, it is determined whether or not the fog occurrence has been determined at step S220 shown in FIG. 6. When it is determined that the window glass 12 is not fogged at step S400, the fog-restricting control operation from step S410 to step S510 is performed.

On the other hand, when it is determined that the window glass 12 is fogged at step S400, a control mode for removing the fog is performed at step S520. Namely, the air suction mode is compulsively switched to the outside air mode, and a blower level of the blower 37 is increased by six levels. Moreover, the blowing-out mode is switched to the defroster mode.

Here, the blower level corresponds to a motor-applying voltage level of the blower 37. The volume of air blown by the blower 37 is increased or decreased in response to the increase or decrease of the motor-applying voltage level. As such, the blower level corresponds to the volume of air blown by the blower 37.

By the control operation of step S520, the outside air having low humidity is introduced in and heated in the a/c interior unit 30. Further, the heated air is blown out from the defroster blowing-out opening 48 toward the inner surface 12a of the window glass 12. Moreover, the amount of this heated air is increased. As a result, the window glass surface relative humidity RHw is smoothly lowered, so the fog of the window glass 12 is removed.

Figure 13:
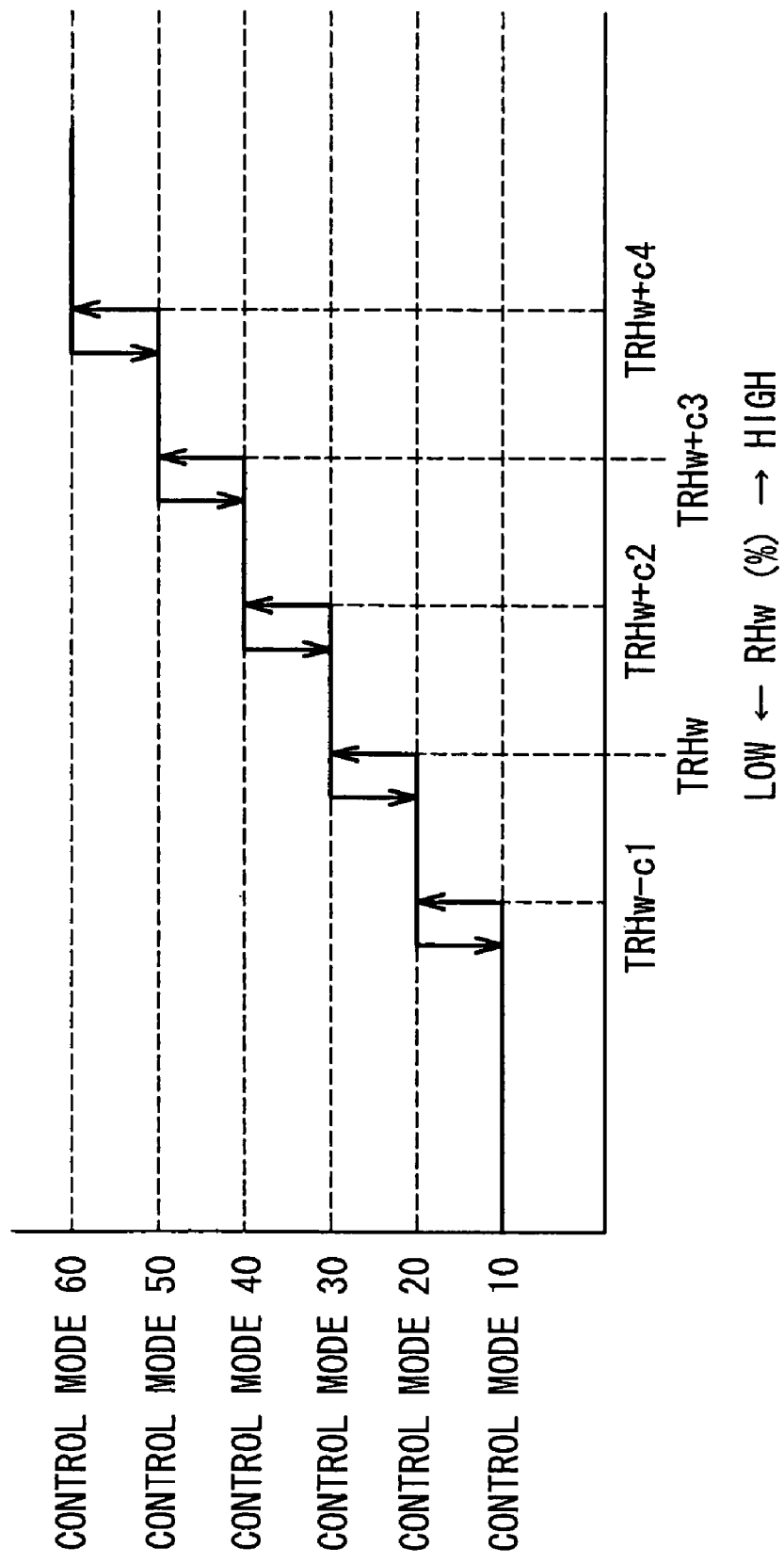
FIG. 13 is a characteristic diagram showing a relationship between the window glass surface relative humidity and fog-restriction control modes according to the first embodiment.

On the other hand, at steps S410, S420, S430, S440, S450, control modes 10, 20, 30, 40, 50 will be respectively determined according to the window glass surface relative humidity RHw, as shown in a map of FIG. 13. In an example shown in FIG. 13, the target window glass surface relative humidity TRHw (for example, 85%) and four judgment threshold values are set. Further, one of six control modes 10, 20, 30, 40, 50, 60 is selected based on a change of the window glass surface relative humidity RHw. The four judgment threshold values are set by increasing or decreasing predetermined amounts c1, c2, c3, c4 with respect to the target window glass surface relative humidity TRHw. That is, the five judgment threshold values are respectively set as TRHw-c1, TRHw, TRHw+c2, TRHw+c3, and TRHw+c4.

As shown in FIG. 12, at steps S460, S470, S480, S490, S500, S510, the selected control modes 10, 20, 30, 40, 50, 60 are respectively performed. When the control mode 10 is determined at step S410, the control mode 10 is performed at step S460. Namely, at step S460, a normal automatic control is performed. When the control mode 20 is determined at step S420, the control mode 20 in which the air suction mode is set to the outside air mode is performed at step S470.

When the control mode 30 is determined at step S430, the control mode 30 in which the blower level is increased by three levels is performed at step S480. When the control mode 40 is determined at step S440, the control mode, 40 in which the blowing-out mode is transited is performed at S490. When the control mode 50 is determined at step S450, the control mode 50 in which the blower level is further increased by three levels is performed at step S500.

When the control mode 50 is not determined at step S450, the control mode 60 is performed at step S510. Namely, at step S510, the inside air mode is compulsively switched to the outside air mode in the case where the inside air mode is manually set.

In steps S460, 470, 480, 490, 500, 510, the symbol "AUTO" represents the normal automatic control mode in which the air suction mode, the blower level, and the blowing-out mode are respectively controlled based on a target blowing-out temperature TAO of the air blown into the passenger compartment. The symbol "FACE" represents a face mode in which air is blown out through the face blowing-out opening 49. The symbol "B/L" represents a bi-level mode in which air is blown out through both the face blowing-out opening 49 and the foot blowing-out opening 50.

Also, the symbol "FOOT" represents a foot mode in which air is blown out through the foot blowing-out opening 50. The symbol "F/D" represents a foot and defroster mode in which air is blown out through both the foot blowing-out opening 50 and the defroster blowing-out opening 48. The symbol "DEF" represents a defroster mode in which air is blown out through the defroster blowing-out opening 48.

The blowing-out mode transition in the control mode 40 of step S490 is performed as below. That is, when the blowing-out mode before the control mode is shifted to the control mode 40 is the foot and defroster mode, the blowing-out mode is transferred to the defroster mode. When the blowing-out mode before the control mode is shifted to the control mode 40 is other than the foot and defroster mode, the blowing-out mode is transferred to the foot and defroster mode. Then, when the blowing-out mode is transferred to the foot and defroster mode in the control mode 40, the F/D mode is maintained even if the state of the control mode 40 is continued.

At steps S460, S470, S480, S490, S500 shown in FIG. 12, when the inside air mode is manually set, the air suction mode is maintained in the inside air mode. According to the anti-fog control operation with reference to FIGS. 12 and 13, the control mode can be sequentially switched from the control mode 10 to the control mode 60 in response to the increase of the window glass surface relative humidity RHw. That is, the control mode is switched so that the effect of reducing the window glass surface relative humidity RHw increases. Therefore, the fog of the window glass 12 can be automatically and effectively removed and restricted.

Figure 14:
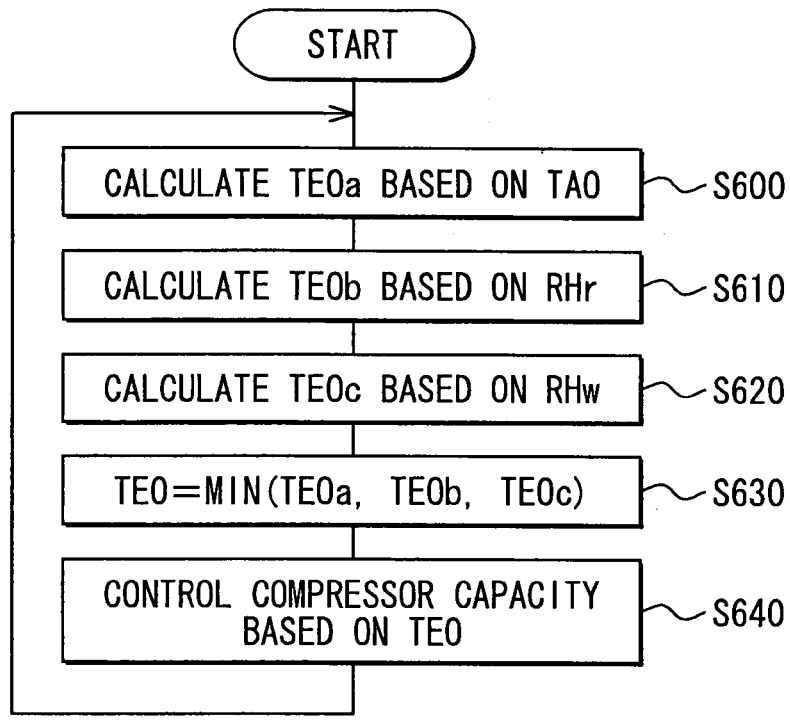
FIG. 14 is a flow chart showing exemplary logic of a control of a compressor according to the first embodiment.

FIG. 14 shows a control routine of the compressor 40. The control operation of the compressor 40 is basically similar to what disclosed in Japanese Patent No. 3309528, and a summary thereof will be described hereafter.

First, at step S600, a target evaporator temperature TEOa, that is, a target temperature of cooling heat exchanger 38 is calculated based on the target blowing-out temperature TAO of air blown into the passenger compartment for controlling the passenger compartment temperature.

Specifically, the target evaporator temperature TEOa is calculated in such a manner that the target evaporator temperature TEOa increases from a minimum temperature (for example, 3° C.) to a maximum temperature (for example, 11° C.) as the target blowing-out temperature TAO increases.

The target blowing-out temperature TAO is an interior blowing-out air temperature (i.e., blowing-out air temperature in passenger compartment) that is necessary to maintain the inside air temperature Tr of the interior of the passenger compartment at a set temperature Tset, which is set through the temperature setting switch 71, irrespective of variation of air conditioner heat loss. As well known, the target blowing-out temperature TAO is calculated based on the set temperature Tset, the outside air temperature Tam, the inside air temperature Tr, and the solar radiation amount Ts.

Then, at step S610, a target evaporator temperature TEOb is calculated based on the passenger compartment humidity RHr detected by the humidity sensor 17 for controlling the humidity inside of the passenger compartment. The target evaporator temperature TEOb is calculated such that the passenger compartment humidity RHr is maintained within a predetermined comfortable range, for example, a range between 50% and 60%.

Therefore, when the passenger compartment humidity RHr is equal to or higher than the comfortable range, for example, 60%, the value of the temperature TEOb will be changed to the low temperature side. On the other hand, when the passenger compartment humidity RHr is equal to or lower than the comfortable range, for example, 50%, the value of the temperature TEOb will be changed to the high temperature side.

Thereafter, at step S620, a target evaporator temperature TEOc for the anti-fog control operation is calculated. The temperature TEOc is calculated such that the anti-fog control operation can be performed based on a cooling (dehumidifying) performance of the evaporator 38.

Specifically, the target evaporator temperature TEOc is set as an evaporator temperature so that the window glass surface relative humidity RHw can be maintained between the target window glass surface relative humidity TRHw and the relative humidity TRHw-b of FIG. 11. The target evaporator temperature TEOc can be obtained based on the glass temperature, the relative humidity TRHw and TRHw-b1, and the relative humidity (substantially equal to 95%) of air blown out from the evaporator 38 according to the wet air diagram.

Then, at step S630, the minimum temperature of the target evaporator temperatures TEOa, TEOb and TEOc is calculated as a final target evaporator temperature TEO. At step S640, the power of the compressor 40 is controlled based on the final target evaporator temperature TEO, by comparing the target evaporator temperature TEO with the evaporator blowing-out air temperature Te detected by the evaporator temperature sensor 64.

That is, when the evaporator blowing-out air temperature Te exceeds the target evaporator temperature TEO, the electromagnetic clutch 40a is energized to actuate the compressor 40 (compressor ON). On the other hand, when the evaporator blowing-out air temperature Te reduces equal to or lower than a temperature TEO-z that is lower than the target evaporator temperature TEO by a predetermined temperature z (e.g., 1° C.), the compressor 40 is stopped (compressor OFF).

Because the actuation of the compressor 40 is intermittently controlled in the above-described manner, the actual evaporator blowing-out air temperature Te is controlled to approximate to the target evaporator temperature TEO. Moreover, the target evaporator temperature TEO is set to the minimum one of the target evaporator temperature TEOa used for the passenger compartment temperature control, the target evaporator temperature TEOb used for the passenger compartment humidity control, and the target evaporator temperature TEOc used for the anti-fog control. Therefore, the passenger compartment temperature, the passenger compartment humidity, and the anti-fog operation can be controlled while controlling the cooling degree of the evaporator 38 according to the power control of the compressor 40.

In the above-described power control of the compressor 40, a fixed capacity type compressor is used as the compressor 40, and an operation rate of the compressor 40 is changed by the intermittent operation of the fixed capacity type compressor. Alternatively, a variable capacity type compressor can be used as the compressor 40. In this case, the power control of the compressor 40 is performed by changing the discharge amount of the refrigerant.

The term "target evaporator temperature" represents a target value of a cooling degree of the evaporator 38. The cooling degree of the evaporator 38 can be measured based on a fin surface temperature of the evaporator 38, in addition to the above-described evaporator blowing-out air temperature Te.

Next, features and effects of the first embodiment will be described. First, the humidity detecting apparatus 10 includes the humidity sensor 17 for detecting the relative humidity of the inside air inside of the passenger compartment, the air temperature sensor 18 for detecting the temperature of the inside air, the glass temperature sensor 23 for detecting the temperature of the window glass 12, the glass surface relative humidity calculation unit 20d, S50 for calculating the glass surface relative humidity based on the output values of the humidity sensor 17, the air temperature sensor 18 and the glass temperature sensor 23. Further, the heat conduction member 15, such as the glass-side heat conduction member 15a and the sensor-side heat conduction member 15b, is provided between the window glass 12 and the glass temperature sensor 23.

As such, the window glass surface relative humidity, which is correlated to the fog of the window glass 12, can be calculated. Therefore, the anti-fog control of the air conditioner is effectively performed using the calculated window glass surface relative humidity. Also, in the method in which the glass temperature is directly detected, since the heat conductive member 15 is provided between the window glass 12 and the glass temperature sensor 23, stress caused when attaching the humidity detecting apparatus 10 to the window glass 12 is absorbed by the heat conductive member 15. Therefore, it is less likely that the soldered portions of the circuit board 14 and the sensors on the circuit board 14 will be affected by the stress. In addition, since the glass temperature sensor 23 is pressed against the heat conductive member 15, heat is effectively conducted through contact surfaces between them. Accordingly, the glass temperature is accurately detected.

Also, the flat metallic member 16 having high heat conductivity is provided between the window glass 12 and the glass temperature sensor 23. Further, the heat conductive member 15 is disposed on both sides of the metallic member 16. For example, the glass-side heat conductive member 15a is disposed between the inner surface 12a of the window glass 12 and one surface of the metallic member 16; and the sensor-side heat conductive member 15b is disposed between the opposite surface of the metallic member 16 and the circuit board 14. This structure will not affect the heat detection in the contact manner, and the stress is absorbed by the metallic member 16. As such, the circuit board 14 and the soldering portions thereon will not be affected by the stress.

Further, the humidity sensor 17, the air temperature sensor 18 and the glass temperature sensor 23 are integrated with each other, and hence easily handled and mounted on the inner surface 12a of the window glass 12 such as the windshield. Furthermore, the humidity sensor 17, the air temperature sensor 18 and the glass temperature sensor 23 are all mounted to the same circuit board 14, that is, integrated with the circuit board 14, and hence easily handled.

The humidity detecting apparatus 10 has the case 11, and the humidity sensor 17, the air temperature sensor 18 and the glass temperature sensor 23 are housed in the case 11. Namely, the sensors 17, 18, 23 are housed in the same case 11. Further, the case 11 is adhered to the inner surface 12a of the window glass 12 using the adhesive sheet 13. Thus, the case 11 is easily fixed to a suitable location on the inner surface 12a of the window glass 12.

The metallic member 16 is integrated into the case 11. For example, the metallic member 16 is integrated with the resinous case 11 by insert molding. Therefore, the metallic member 16 is easily handled and manufacturing costs reduce.

The heat conductive member 15, such as the glass-side heat conductive member 15a, is in contact with the inner surface 12a of the window glass 12 and is surrounded by the adhesive sheet 13. That is, the glass-side heat conductive member 15a is disposed in the opening 13a of the adhesive sheet 13. Therefore, even if the adhesion of the glass-side heat conductive member 15a is insufficient, the glass-side heat conductive member 15a can be held without being displaced and dropped.

The arithmetic processing unit 20, which performs calculation based on the output values of the humidity sensor 17, the air temperature sensor 18 and the glass temperature sensor 23, is mounted on the circuit board 14. Also, the arithmetic processing unit 20 is located at the position separated from the humidity sensor 17 on the circuit board 14 as much as possible. For example, the arithmetic processing unit 20 is arranged at the position diagonally opposite to the humidity sensor 17 with respect to the center of the circuit board 14. Therefore, it is less likely that the humidity sensor 17 and the humidity detecting surroundings to be detected by the humidity sensor 17 will be affected by heat generated from the arithmetic processing unit 20. Accordingly, detecting accuracy of the humidity by the humidity sensor 17 improves.

On the circuit board 14, the air temperature sensor 18 are arranged at a position close to the humidity sensor 17. Therefore, the humidity and the temperature are detected in the similar surroundings. Accordingly, the temperature and the humidity are further accurately detected.

The air temperature sensor 18 and the glass temperature sensor 23 are substantially coaxially arranged on opposite sides of the circuit board 14. Therefore, the glass temperature and the temperature of the air adjacent to the window glass 12 are detected at the positions close to each other, by the glass temperature sensor 23 and the air temperature sensor 18. Accordingly, the glass surface relative humidity is further accurately calculated.

Since the circuit board 14 is formed with the slit 14a between the arithmetic processing unit 20 and the glass temperature sensor 23, the transfer of heat from the arithmetic processing unit 20 toward the glass temperature sensor 23 through the circuit board 14 is reduced. That is, it is less likely that the heat of the arithmetic processing unit 20 will affect the glass temperature detected by the glass temperature sensor 23. Accordingly, the glass temperature is further accurately detected.

The humidity detecting apparatus 10 is mounted to the inner surface 12a of the window glass 12. The window glass 12 is, for example, the front windshield of the vehicle. Further, the air conditioner has the defroster blowing-out opening 48 for blowing out the air toward the windshield 12. At least one of the air suction mode control of the inside/outside air switching door 35, the blower level control of the blower 37 and the blowing-out mode control of the blowing-out mode doors 51 to 53 is performed based on the calculated value of the glass surface relative humidity calculation unit 20d, S50.

Namely, in the air conditioner, the anti-fog control operation is automatically performed by executing at least one of the air suction mode control, the blower level control of the blower 37 and the blowing-out mode control based on the glass surface relative humidity. Also, in the air suction mode control, the inside air suction mode and the outside air suction mode are selected such that the inside air ratio increases in the range in which the window glass 12 is not fogged. Therefore, the ventilation heat loss is reduced, and hence the performance of the heating operation improves.

Also, the power of the compressor 40 is controlled such that the actual cooling degree of the evaporator 38 is set to the target value. That is, since the cooling degree of the evaporator 38 is controlled, the glass surface relative humidity is controlled in the predetermined range, and thus the anti-fog control for the window glass 12 is automatically performed.

Second Embodiment

Figure 15:
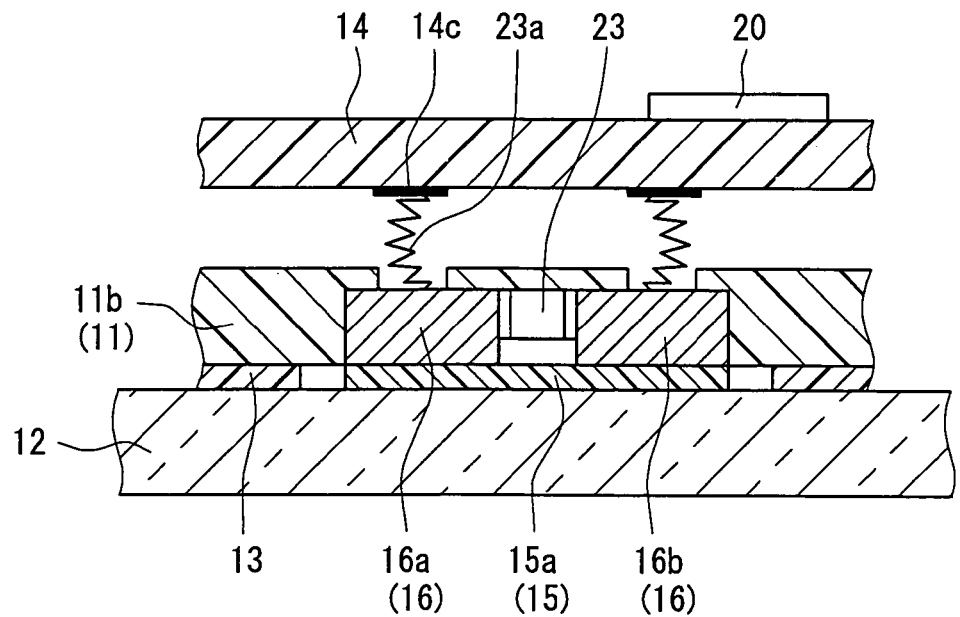
FIG. 15 is a schematic cross-sectional view of a glass temperature detecting portion of a humidity detecting apparatus according to a second embodiment of the present invention.

Next, a second embodiment of the present invention will be described with reference to FIG. 15. FIG. 15 shows a glass temperature detecting part of a humidity detecting apparatus 10 of the second embodiment. Hereafter, like components are denoted by like reference numerals as the first embodiment and a description thereof will not be repeated. Different structures and effects will be mainly described hereafter.

In the second embodiment, the glass temperature sensor 23 is not arranged on the circuit board 14 on which the humidity sensor 17 and the air temperature sensor 18 are mounted. As shown in FIG. 15, the glass temperature sensor 23 is connected to the circuit board 14 through electrically conductive members 23a.

For example, the metallic member 16 is divided into a first metallic part 16a and a second metallic part 16b. The glass temperature sensor 23 is arranged between the first metallic part 16a and the second metallic part 16b. The electrically conductive members 23a are easily deformable member such as springs. The electrically conductive members 23a connect the first and second metallic parts 16a, 16b and electrode portions 14c of the circuit board 14 so that a signal indicative of the temperature detected by the glass temperature sensor 23 is transmitted to the circuit board 14.

The glass-side heat conductive member 15a is adhered to the surfaces of the first and second metallic parts 16a, 16b, which face the inner surface 12a of the window glass 12. Also, the glass-side heat conductive member 15a is disposed in the opening 13a of the adhesive sheet 13 and is adhered to the inner surface 12a of the window glass 12 in a closely contact manner.

Since the glass temperature sensor 23 is arranged at a position separate from the circuit board 14, the heat generated from the arithmetic processing unit 20 is restricted from being transferred to the glass temperature sensor 23 through the circuit board 14. Therefore, it is less likely that the glass temperature detected by the glass temperature sensor 23 will be affected by the heat of the arithmetic processing unit 20. Accordingly, the glass temperature is accurately detected.

Further, the glass temperature sensor 23 is disposed between the plural metallic parts 16a, 16b, and is connected to the circuit board 14 through the plural metallic parts 16a, 16b and the electrically conductive member 23a. As such, it is less likely that the glass temperature sensor 23 will be affected by the heat of the arithmetic processing unit 20. Accordingly, detecting accuracy of the glass temperature sensor 23 further improves.

Third Embodiment

Figure 16:
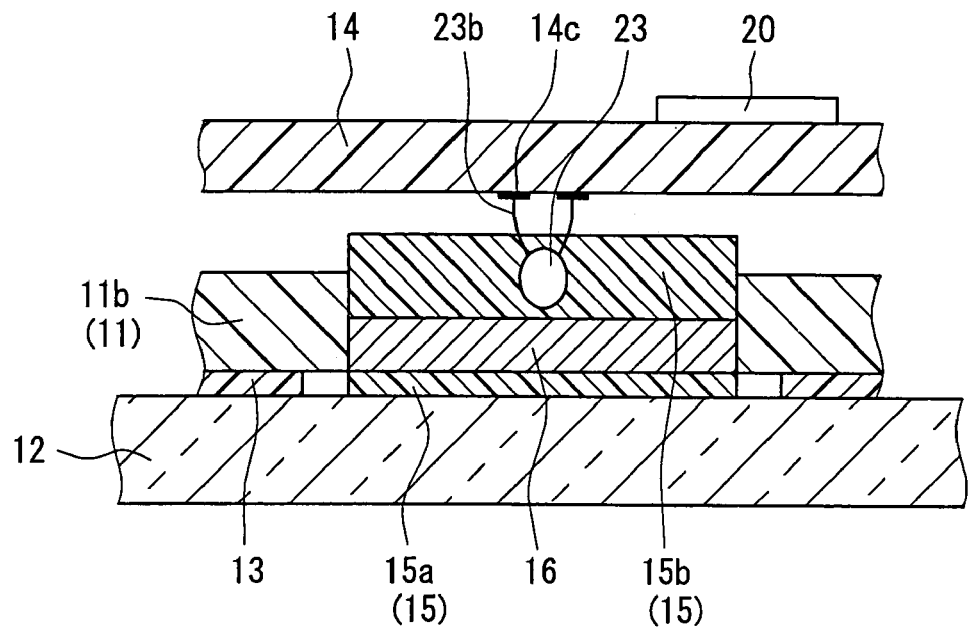
FIG. 16 is a schematic cross-sectional view of a glass temperature detecting portion of a humidity detecting apparatus according to a third embodiment of the present invention.

Next, a third embodiment will be described with reference to FIG. 16. FIG. 16 shows a glass temperature detecting part of a humidity detecting apparatus 10 of the third embodiment. Hereafter, like components are denoted by like reference numerals as the first embodiment and a description thereof will not be repeated. Different structures and effects will be mainly described hereafter.

In the third embodiment, the glass temperature sensor 23 is arranged at a position separate from the circuit board 14 on which the humidity sensor 17 and the air temperature sensor 18 are mounted. As shown in FIG. 16, the glass-side heat conductive member 15a and the sensor-side heat conductive member 15b are disposed on the opposite sides of the metallic member 16. The sensor-side heat conductive member 15b has a thickness such that at least a temperature detecting portion of the glass temperature sensor 23 is embedded therein. For example, the sensor-side heat conductive member 15b is made of heat conductive gel and has the thickness greater than that of the first embodiment. The glass temperature sensor 23 is a lead type glass temperature sensor having lead wires 23b as the electrically conductive members. The lead wires 23b extend from the detecting portion of the glass temperature sensor 23 in the sensor-side heat conductive member 15b and connect to the circuit board 14.

Accordingly, the glass temperature sensor 23 is embedded in the sensor-side heat conductive member 15b, which is disposed on a side opposite to the window glass 12 with respect to the metallic member 16, and electrically connected to the circuit board 14 though the lead wires 23b or the like as the electrically conductive members. As such, it is less likely that the heat generated from the arithmetic processing unit 20 will affect the temperature detecting portion of the glass temperature sensor 23 through the circuit board 14. Therefore, detecting accuracy of the glass temperature sensor 23 further improves.

Other Embodiments

Although the present invention has been fully described in connection with the above exemplary embodiments with reference to the accompanying drawings, it is to be noted that various changes and modifications will become apparent to those skilled in the art.

Figure 17:
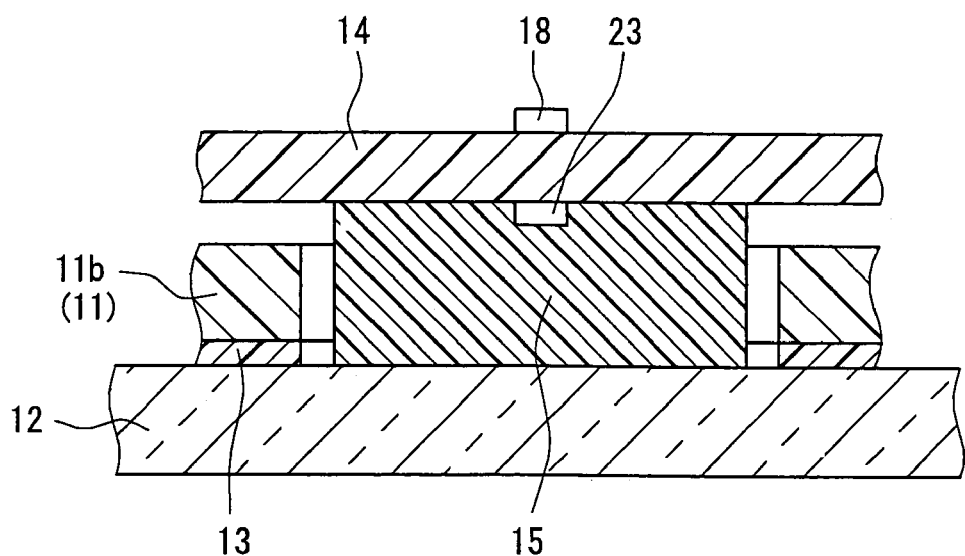
FIG. 17 is a schematic cross-sectional view of a glass temperature detecting portion of a humidity detecting apparatus according to further another embodiment of the present invention.

FIG. 17 shows further another embodiment of the present invention. As shown in FIG. 17, the thickness of the heat conductive member 15 is increased and adhered between the inner surface 12a of the window glass 12 and the second surface of the circuit board 14. The heat conducive member 15 is made of, for example, heat conductive gel. The glass temperature sensor 23 is embedded in the heat conductive member 15. In this case, the heat conductive member 15 absorbs stress. That is, stress applied to the circuit board 14 is absorbed through the heat conductive member 15. Accordingly, detecting accuracy of the glass temperature improves.

In the above embodiments, the relative humidity of the glass surface 12a is calculated using the detected glass temperature. Further, the dew-point temperature of the glass surface 12a may be calculated based on the glass temperature detected by the glass temperature sensor 23 of the above embodiments and the temperature and relative humidity of air on a periphery thereof. Further, the structure of the glass temperature sensor 23 of the above embodiments may be employed to a glass temperature detecting apparatus, instead of the humidity detecting apparatus 10.

Also, the arrangement position of the arithmetic processing unit 20 is not limited to the circuit board 14, which is housed in the case 11 of the humidity detecting apparatus 10. For example, the arithmetic processing unit 20 or the functions thereof may be arranged in the air conditioning control unit 26.

In the above embodiments, the humidity detecting apparatus 10 is exemplarily mounted to the front windshield 12 of the vehicle. However, the humidity detecting apparatus 10 can be mounted to other portions such as a rear window glass of the vehicle. Furthermore, the humidity detecting apparatus 10 can be employed in any purposes other than the detection of humidity of vehicles.

Additional advantages and modifications will readily occur to those skilled in the art. The invention in its broader term is therefore not limited to the specific details, representative apparatus, and illustrative examples shown and described.

What is claimed is:

1. A humidity detecting apparatus, comprising:
   a humidity sensor for detecting a relative humidity of air on an interior side of a window glass;
   an air temperature sensor for detecting a temperature of the air;
   a glass temperature sensor for detecting a temperature of the window glass;
   a glass surface relative humidity calculation unit for calculating a relative humidity of an inner surface of the window glass based on output values of the humidity sensor, the air temperature sensor and the glass temperature sensor;
   a circuit board electrically connected to the glass temperature sensor;
   a first heat conductive member disposed between the window glass and the glass temperature sensor;
   a metallic member having heat conductivity disposed between the circuit board and the window glass; and
   a second heat conductive member, wherein
   the first heat conductive member is disposed between the metallic member and the window glass and the second heat conductive member is disposed between the metallic member and the circuit board, and
   the glass temperature sensor is at least partially embedded in the second heat conductive member.

2. The humidity detecting apparatus according to claim 1, wherein the metallic member has a flat shape, and the first and second heat conductive members are disposed to be in contact with surfaces of the metallic member, respectively.

3. The humidity detecting apparatus according to claim 1, wherein
   the humidity sensor, the air temperature sensor and the glass temperature sensor are integrated into a unit on the inner surface of the window glass.

4. The humidity detecting apparatus according to claim 3, wherein the humidity sensor, the air temperature sensor and the glass temperature sensor are mounted to the circuit board.

5. The humidity detecting apparatus according to claim 3, wherein
   the humidity sensor and the air temperature sensor are mounted to the circuit board, and the glass temperature sensor is disposed at a position separate from the circuit board and is electrically connected to the circuit board through a deformable and electrically conductive member.

6. The humidity detecting apparatus according to claim 5, wherein the metallic member includes a first metallic part and a second metallic part, the first and second metallic parts are disposed along the first heat conductive member, and the glass temperature sensor is disposed between the first and second metallic parts such that a signal indicative of temperature detected by the glass temperature sensor is transmitted to the circuit board through at least one of the first and second metallic parts.

7. The humidity detecting apparatus according to claim 5, wherein the electrically conductive member extends from the embedded glass temperature sensor and connects to the circuit board.

8. The humidity detecting apparatus according to claim 1, further comprising:

a case disposed on the inner surface of the window glass, wherein the humidity sensor, the air temperature sensor and the glass temperature sensor are housed in the case.

9. The humidity detecting apparatus according to claim 8, wherein the metallic member is disposed between the window glass and the glass temperature sensor, and the metallic member is integrated into the case.

10. The humidity detecting apparatus according to claim 8, further comprising:

an adhesive sheet disposed between the inner surface of the window glass and the case such that the case is adhered to the inner surface of the window glass through the adhesive sheet.

11. The humidity detecting apparatus according to claim 10, wherein the first heat conductive member is in contact with the inner surface of the window glass and surrounded by the adhesive sheet.

12. The humidity detecting apparatus according to claim 1, wherein the circuit board includes an arithmetic processing unit, the glass surface relative humidity calculation unit is included in the arithmetic processing unit, and the humidity sensor is mounted on the circuit board at a position opposite to the arithmetic processing unit with respect to a center portion of the circuit board.

13. The humidity detecting apparatus according to claim 12, wherein the air temperature sensor is mounted on the circuit board at a position adjacent to the humidity sensor.

14. The humidity detecting apparatus according to claim 12, wherein the air temperature sensor and the glass temperature sensor are mounted on opposite surfaces of the circuit board and are substantially coaxially aligned.

15. The humidity detecting apparatus according to claim 12, wherein the glass temperature sensor is mounted on the circuit board, and the circuit board is formed with a slit between the arithmetic processing unit and the glass temperature sensor.

16. An air conditioner for a vehicle, comprising:

an inside/outside air switching device operable to open and close an inside air suction port and an outside air suction port for switching an air suction mode;

a blower for blowing air drawn from at least one of the inside air suction port and the outside air suction port;

a cooling heat exchanger for cooling air blown by the blower;

a heating heat exchanger for heating air blown by the blower;

a plurality of blowing-out openings through which air, a temperature of which has been controlled through the cooling heat exchanger and the heating heat exchanger, is blown into a passenger compartment of the vehicle, at least one of the plurality of blowing-out openings being a defroster blowing-out opening through which the air is blown toward a windshield of the vehicle;

a blowing-out mode door operable to open and close at least the defroster blowing-out opening for switching a blowing-out mode;

the humidity detecting apparatus according to claim 1; and a control unit adapted to control at least one of the inside/outside air switching device, the blower and the blowing-out mode door based on the relative humidity calculated by the glass surface relative humidity calculation unit, wherein the window glass is the windshield of the vehicle, and the humidity detecting apparatus is disposed on an inner surface of the windshield.

17. The air conditioner according to claim 16, further comprising:

a compressor for circulating a refrigerant through the cooling heat exchanger, wherein the control unit is adapted to determine a target value of a cooling degree of the cooing heat exchanger such that the glass surface relative humidity is in a predetermined range, and to control a power of the compressor such that the cooling degree of the cooling heat exchanger is maintained to the target value.

* * * * *